United States Patent
Eklund et al.

(10) Patent No.: US 9,712,033 B2
(45) Date of Patent: Jul. 18, 2017

(54) SYSTEM AND METHOD FOR STABILIZING A VOICE COIL

(71) Applicant: Mindray Medical Sweden AB, Sundbyberg (SE)

(72) Inventors: Mathias Eklund, Stockholm (SE); Göran Cewers, Limhamn (SE)

(73) Assignee: SHENZHEN MINDRAY BIO-MEDICAL ELECTRONICS CO., LTD, Shenzhen (CN)

( * ) Notice: Subject to any disclaimer, the term of this patent is extended or adjusted under 35 U.S.C. 154(b) by 17 days.

(21) Appl. No.: 14/869,815

(22) Filed: Sep. 29, 2015

(65) Prior Publication Data

US 2016/0094116 A1 Mar. 31, 2016

(30) Foreign Application Priority Data

Sep. 30, 2014 (EP) .................................... 14186934

(51) Int. Cl.
| | |
|---|---|
| *H02K 33/00* | (2006.01) |
| *H02K 41/035* | (2006.01) |
| *A61M 16/20* | (2006.01) |
| *H02P 25/028* | (2016.01) |
| *H02P 25/034* | (2016.01) |
| *F16F 15/02* | (2006.01) |
| *F16K 31/06* | (2006.01) |

(52) U.S. Cl.
CPC ......... *H02K 41/0354* (2013.01); *A61M 16/20* (2013.01); *A61M 16/203* (2014.02); *H02P 25/028* (2013.01); *H02P 25/034* (2016.02); *A61M 16/205* (2014.02); *F16F 15/02* (2013.01); *F16K 31/06* (2013.01)

(58) Field of Classification Search
CPC . H02K 41/0354; A61M 16/203; A61M 16/20; A61M 16/205; H02P 25/034; H02P 25/028; F16F 15/02; F16K 31/06
USPC ........ 318/135, 119, 21, 35, 37, 127, 400.04, 318/400.34; 128/205.24, 205.19, 204.21, 128/207.21, 200.24; 360/75
See application file for complete search history.

(56) References Cited

U.S. PATENT DOCUMENTS

| | | | | |
|---|---|---|---|---|
| 5,127,400 A | * | 7/1992 | DeVries | A61M 16/20 128/204.23 |
| 5,339,807 A | * | 8/1994 | Carter | A61M 16/205 128/204.21 |
| 5,771,884 A | * | 6/1998 | Yarnall | A61M 16/20 128/204.19 |
| 5,927,275 A | * | 7/1999 | Loser | A61M 16/205 128/204.21 |
| 6,886,801 B2 | * | 5/2005 | Hallback | F16K 31/084 251/129.15 |
| 6,922,302 B2 | * | 7/2005 | Kusumoto | G11B 5/54 360/69 |
| 7,235,938 B2 | * | 6/2007 | Daio | G11B 5/5526 318/400.34 |

(Continued)

*Primary Examiner* — Rita Leykin
(74) *Attorney, Agent, or Firm* — Kory D. Christensen; Polsinelli LLP

(57) ABSTRACT

A device or method for stabilizing a voice coil is disclosed. The device comprises a voice coil for providing a motive force, and means for measuring a signal from said voice coil related to a motional electromotive force. The device further comprises a unit for controlling an amplification of said signal to create a force in said voice coil in a direction of said motional electromotive force.

16 Claims, 3 Drawing Sheets

(56) References Cited

U.S. PATENT DOCUMENTS

| | | | | |
|---|---|---|---|---|
| 7,421,359 B2* | 9/2008 | Harmer | ............... | G11B 5/5534 |
| | | | | 318/628 |
| 7,486,039 B2* | 2/2009 | Berto | .................... | H02P 25/034 |
| | | | | 318/400.34 |
| 7,800,857 B1* | 9/2010 | Calaway | ................ | G11B 5/596 |
| | | | | 360/75 |
| 8,973,578 B2* | 3/2015 | Dellaca' | ............ | A61M 16/0051 |
| | | | | 128/204.18 |
| 2005/0134374 A1* | 6/2005 | Hench | ....................... | H03F 1/08 |
| | | | | 330/86 |
| 2007/0205674 A1* | 9/2007 | Tseng | ....................... | G03B 3/10 |
| | | | | 310/14 |
| 2009/0223513 A1* | 9/2009 | Papania | ............ | A61M 15/0065 |
| | | | | 128/200.16 |
| 2010/0170512 A1* | 7/2010 | Kuypers | ............... | A61M 16/20 |
| | | | | 128/204.23 |
| 2013/0167843 A1* | 7/2013 | Kimm | ................ | F16K 31/1266 |
| | | | | 128/205.24 |
| 2014/0283831 A1* | 9/2014 | Foote | ................ | A61M 16/009 |
| | | | | 128/204.19 |
| 2015/0346699 A1* | 12/2015 | Li | ......................... | G05B 11/32 |
| | | | | 318/650 |
| 2015/0352302 A1* | 12/2015 | Kuypers | ............... | A61M 16/20 |
| | | | | 128/204.23 |

* cited by examiner

SYSTEM AND METHOD FOR STABILIZING A VOICE COIL

BACKGROUND OF THE INVENTION

Field of the Invention

This disclosure pertains in general to voice coil motors. More particularly the disclosure relates to controlling a voice coil, such as stabilizing a voice coil for providing a motive force, such as stabilizing a voice coil motor. In particular this relates to voice coil motors for controlling an inspiration or expiration valve for medical ventilators, anaesthesia machines or anaesthesia monitoring.

Description of the Prior Art

To control the expiratory pressure (PEEP) a voice coil motor which controls a disc valve is a common solution. In this kind of valve the expiratory pressure is more or less proportional to the force from the voice coil. Also the force from the voice coil is ideally proportional to the current through the windings in the voice coil.

The above model is very simplified. In an actual application, the flow through the valve may vary due to the breathing pattern. This will create a movement of the disc to compensate for the varying flow. The mass of the moving parts will have an inertia which will affect the force balance in the valve. Other characteristics with the current technology are that membranes inside the valve may create spring forces and the voice coil is not ideal.

A significant drawback with this kind of valve is that it is not stable. A valve that is not stable will vibrate and consequently cause oscillations in the flow and pressure. There are several known ways to try to stabilize the valve. Using normal pressure or flow feedback to stabilize the valve is complicated since the oscillations can be fast and it is difficult to make any conclusion of the movement of the valve just by measuring the pressure or flow. Using friction is another way to prevent oscillations, but it is not desired since it may make the PEEP pressure control inferior. Other possibilities are for examples viscous damping, i.e. an opposing force proportional to the speed of the voice coil, using electromagnets or ferrofluids. A major drawback with conventional viscous damping is that the viscous damping coefficient is constant while the actual needed damping varies a lot depending on the pressure and also on the flow. The damping needed for a high pressure is several times larger than what is needed for a low pressure. The drawback with having a too high damping coefficient is that the valve responds slowly to control signals as well as to changes in the flow rate which can result in that the valve will not be able to control a constant PEEP pressure. Using a low constant viscous damping coefficient would mean that the system would be unstable for high pressures, while using a high damping coefficient would mean that the valve would respond too slowly for low pressures. Further possibilities are positional or velocity feedback by use of a positional or velocity sensor, with the drawbacks of increased cost and complexibility.

U.S. Pat. No. 5,127,400 A and U.S. Pat. No. 5,339,807 A discloses systems using a complex mechanical design wherein a separate permanent magnet is fixed to the shaft of the voice coil motor in such a way that it will move inside a separate stationary coil as a sensor for the motional EMF.

A voice coil motor may also be used for controlling other parameters than the PEEP, such as the pressure and flow during inspiration. When controlling, for example, the pressure and the flow during inspiration using a voice coil motor the system also demonstrates issues with stabilization.

It would not be straight forward to control the expiratory pressure, for example, by just changing the current to achieve a desired PEEP. Achieving a correct pressure demands an improved feedback system. Hence, a new improved design of the control of the feedback system with a better capability to avoid oscillations but still fast enough to ensure that the expiratory pressure quickly can reach the desired PEEP for different patient categories as well as different environmental parameters. It would in particularly be advantageous to have a damping that could be optimized and adjusted depending on environmental parameters, such as pressure or flow.

SUMMARY OF THE DISCLOSURE

Accordingly, embodiments of the present disclosure preferably seek to mitigate, alleviate or eliminate one or more deficiencies, disadvantages or issues in the art, such as the above-identified, singly or in any combination by providing a device, system or method according to the appended patent claims for providing an improved voice coil motor and thereby an improved pneumatic valve. These voice coils may, for example, be used for controlling an inspiration or expiration valve for medical ventilators, anaesthesia machines or anaesthesia monitoring.

According to one aspect of the disclosure, a device for stabilizing voice coil, such as stabilizing a voice coil motor, is described. The device comprises a voice coil for providing a motive force. The device may further include means for measuring a signal from the voice coil related to a motional electromotive force, and a unit for controlling an amplification of the signal to create a force in said voice coil in a direction of said motional electromotive force.

The device may be used for controlling an inspiration or expiration valve by stabilizing a voice coil used for providing a motive force, such as stabilizing a voice coil motor, used as an actuator. The valves may be used for medical ventilators, anaesthesia machines or anaesthesia monitoring.

Some advantages are that this device and method provides a way to adjust and optimize the damping of the voice coil used for providing a motive force depending on the environment, such as different pressure and/or fluid flow. Adjusting and optimizing the damping provides a stable and effective control of different parameters, such as PEEP-pressure or the inspiratory flow and/or pressure. An effective control of the PEEP-pressure or the inspiratory flow and/or pressure may generate improved ventilation and provides for a low work of breathing for the patient. Another advantage is that the device and method is easily implanted without adding any further sensors to the system. The only further sensor that may need to be added is a sense resistor which could be disregarded compared to the sensors of the prior art systems.

In some examples of the disclosure is the signal measured by measuring a current through the voice coil used for providing a motive force, such as a voice coil of a voice coil motor. The measured current through the voice coil is due to a motional electromotive force (motional EMF) generated when either the voice coil or an associated magnet is moving.

In some examples of the disclosure is the amplified current signal controlled by controlling a set voltage to the voice coil, such as the voice coil of a voice coil motor.

In some examples of the disclosure is a sense resistor connected in series with the voice coil used for providing a motive force, such as voice coil of a voice coil motor, to measure a voltage. The current is calculated based on the voltage and a resistance of the sense resistor.

In some examples of the disclosure is the signal a current error based on a difference between an estimated or calculated current in steady state and a measured current related to a generated motional EMF. The voice coil is in steady-state when neither the voice coil nor an associated magnet moves, hence no motional EMF is generated.

In some examples of the disclosure is the current error amplified by changing the set voltage resulting in a change of the current through the voice coil.

In some examples of the disclosure is the signal measured by measuring a voltage across the voice coil. The measured voltage through the voice coil is due to a motional electromotive force (motional EMF) generated when either the voice coil or an associated magnet is moving.

In some examples of the disclosure is the amplified voltage signal controlled by controlling a set current to the voice coil.

In some examples of the disclosure is the signal a voltage error based on a difference between a measured or estimated voltage across the voice coil in steady state and a measured voltage related to a generated motional EMF. The voice coil is in steady-state when neither the voice coil nor an associated magnet moves, hence no motional EMF is generated.

In some examples of the disclosure is the voltage error amplified by changing the set current, resulting in a change of the voltage across the voice coil.

In some examples of the disclosure is the controlling of the amplified signal performed directly or by a pulse-width modulator.

In some examples of the disclosure is a negative gain used to cancel out or lessen effects of inherent motional electromotive force in the voice coil.

In some examples of the disclosure is a high-pass filter used to remove DC and low frequency components before amplification of the error signal.

In a further aspect of the disclosure, a method of stabilizing a voice coil is described. The method comprising, measuring a signal related to a motional electromotive force of a voice coil, controlling an amplification of the signal to create a force in the voice coil in a direction of the motional electromotive force.

In some examples of the disclosed method is the signal a current error based on a difference between an estimated or calculated current in steady state and a measured current related to a generated motional EMF.

In some examples of the disclosed method is the signal a voltage error based on a difference between an estimated or calculated voltage in steady state and a measured voltage related to a generated motional EMF.

Damping is herein defined as a force which is directed in the opposite direction of a movement and which has a stabilizing effect.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which examples of the disclosure are capable of will be apparent and elucidated from the following description of embodiments of the present disclosure, reference being made to the accompanying drawings, in which.

DESCRIPTION OF EMBODIMENTS

Specific examples of the disclosure will now be described with reference to the accompanying drawings. This disclosure may, however, be embodied in many different forms and should not be construed as limited to the examples set forth herein; rather, these examples are provided so that this disclosure will be thorough and complete, and will fully convey the scope of the disclosure to those skilled in the art.

While several examples of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. The scope of the disclosure is only limited by the appended patent claims.

The movement of the coil within a magnetic field creates a motional electromotive force (motional EMF, sometimes also referred to as back EMF) which is a voltage across the coil that creates a current in the coil so that the direction of the force created by this current may be opposite to that of the movement. The motional electromotive force (motional EMF) may be seen as a viscous damping as the force is proportional to the speed of the movement of the coil inside the magnetic field of the voice coil.

A force which is directed in the opposite direction of a movement has a stabilizing effect (i.e. damping).

The damping caused by the motional electromotive force is normally not strong enough to stabilize the valve/coil, and it is not possible to adjust the damping coefficient, such as the strength of the dampening.

Figure 1:
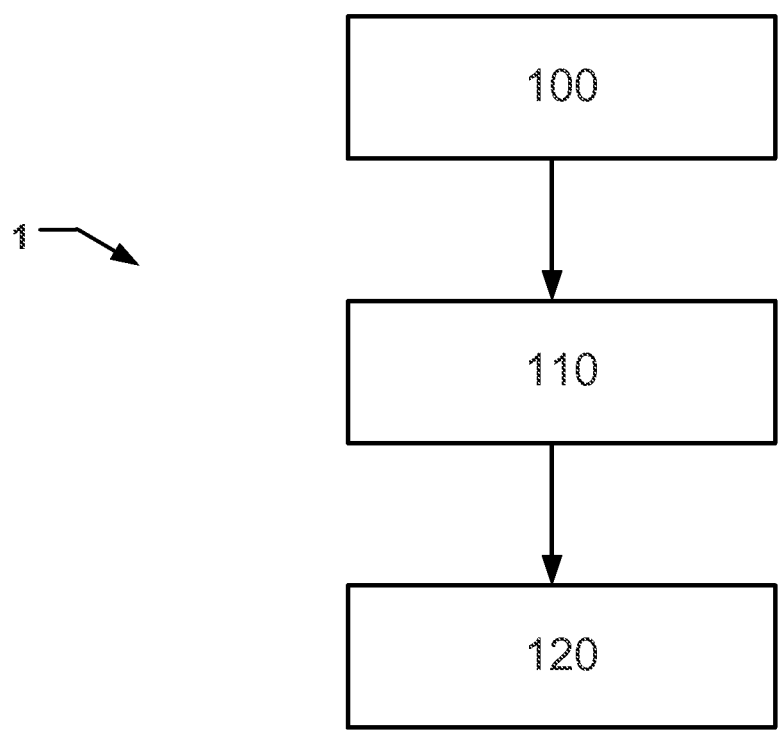
FIG. 1 is illustrating a flow chart of a device for stabilizing a voice coil.

FIG. 1 is illustrating a flow chart of a device 1 for stabilizing a voice coil for providing a motive force, such as a voice coil in a voice coil motor. In the device illustrated in the flow chart, means are used for measuring a signal 100 related to the motional EMF, caused by the movement of the coil inside the magnetic field or by an associated magnet.

The measured signal related to a motional EMF may include two components; a first component related to the motional EMF, and a second component related to a drive current or a drive voltage through the voice coil for providing a motive force.

Alternatively, in examples were an external force is moving the voice coil or an associated magnet, the measured signal related to a motional EMF may include at least one component related to the motional EMF.

The measured signal is amplified 110 and controlled 120 in order to create an extra force in the same direction as the motional EMF, thereby increase the damping of the movement of the coil, and thereby suppress any instability (oscillations) of the voice coil.

This has been realized by controlling the set voltage to the voice coil. The controlling may be done either directly or preferably by a Pulse-width modulator (PWM). The current through the voice coil is measured for example by using a sense resistor in series with the voice coil and measure the voltage across the sense resistor.

The current in the voice coil during steady state can be estimated, since the set voltage is known, if the resistance and the inductance of the system also are known, or if the resistance and the inductance may be estimated. When either the voice coil or an associated magnet moves, the motional EMF may create a voltage opposing that of the movement, which will result in a change of the current through the voice coil. The change may be an increase or a decrease of the voltage depending on the direction of the motion. The difference between a desired current (in steady state) and the measured current, i.e. the current error, is proportional to the motional EMF and thereby also to the movement of either the voice coil or an associated magnet, such as the movement of a voice coil or an associated magnet in a voice coil motor.

This current error can then be amplified by changing the set voltage correspondingly and thereby change the current in the voice coil so that the change in the set voltage may in fact result in a change in force in the same direction as the motional EMF.

Alternatively, in some examples, another way to realize this could be to control a voice coil, such as a voice coil motor, with a set current and by measuring the voltage across the coil. A voltage error is then calculated in a similar way as the current error above. The voltage error results from a difference between a desired voltage when the voice coil is in steady state (which may be estimated similarly to the estimation of the current in the voice coil during steady state) and a measured voltage related to the motional EMF which is measured when either the voice coil or the associated magnet is moving. The motional EMF may then be controlled by amplification of any change in voltage due to movement of the voice coil by changing the set current of the voice coil.

This allows the viscous damping constant to be changed depending on the pressure in the valve or the flow through the valve, simply by changing the gain of the amplification of the current error or voltage error, and thereby achieve optimal damping so that the valve may be stable and still have good performance for different working conditions.

Additionally, the same principle may be used to cancel out or lessen the effect of inherent motional EMF in a voice coil for providing a motional force, simply by using a negative gain (it must be less than −1). This may be useful if the valve needs to open or close as quick as possible, or if the inherent damping is too large for low pressure.

The resistance of the system may not be exactly known and that the resistance may change due to heating. Hence, this may result in a current error or a voltage error from other sources than motional EMF. For that reason it is necessary to remove the DC and low frequency components of the current error or voltage error by use of a high-pass filter before the amplification of the signal. Depending on the system noise the current error or voltage error may or may not need extra filtering to remove the noise which otherwise may cause oscillation of the voice coil providing a motive force.

Figure 2:
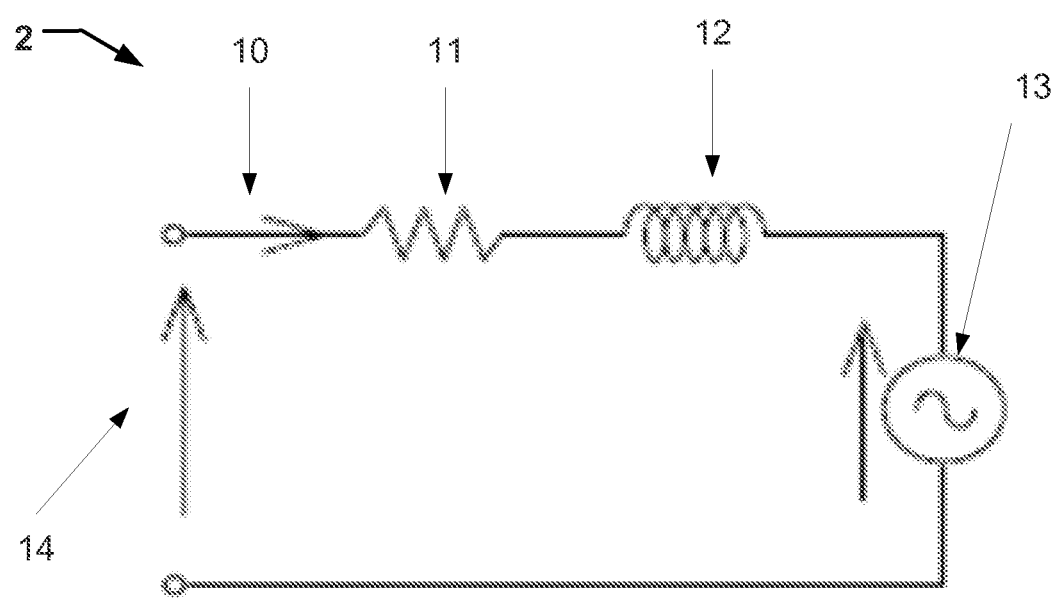
FIG. 2 is illustrating an example of an electrical model of a voice coil.

FIG. 2 illustrates an example of an electrical model 2 of a voice coil. In this model 2, the voice coil may be described as a resistance (R) 11 in series with an inductance (L) 12 and a voltage source ($e_m$) 13. The voltage source 13 is called motional electromotive force (EMF), and is caused by the movement of the coil inside the magnetic field. The figure also illustrates the set voltage (V) 14 and the current (i) 10. The circuit equation can be written as:

$$V - e_m = Ri + L\frac{di}{dt}$$

Because of the inductance, 12, of the voice coil, any change in current 10 through the voice coil will also cause a voltage or electromotive force which opposes this change in current 10. This effect is not due to the movement of the coil inside the magnetic field and is a completely separate effect caused by the inductance 12. Also, depending on the electrical and magnetic design of the voice coil motor, the inductance 12 may or may not be constant, and may have a frequency and coil position dependency. A variable inductance 12 may also affect the voltage 13. In order to distinguish the current (or voltage) change caused by the coil motion from other effects it is important to separate them. The resistance 11 and inductance 12 of the voice coil is defined by the design of the voice coil and can therefore be characterized. Since the resistance 11 and inductance 12 of the voice coil is known or can be estimated, it is straight forward to calculate the estimated current through the voice coil in the case of a change in the set voltage 14. In the same way is it straight forward to estimate the effect on the current due to the change in the motional EMF 13 caused by a movement of the coil inside the magnetic field.

If the current is estimated for a voice coil in steady state then any difference between this estimated current and the measured current is related to the change in the motional EMF 13 due to the actual movement of the coil inside the magnetic field (providing that the current has been estimated and measured correctly). This difference between the estimated current and the measured current is then amplified to obtain the damping effect.

The electrical model in FIG. 2 is used to illustrate the principle when using a set voltage. Similar illustration may be used when using a set current. In this case, any difference between the estimated voltage and the measured voltage is due to the change in the motional EMF 13.

Figure 3:
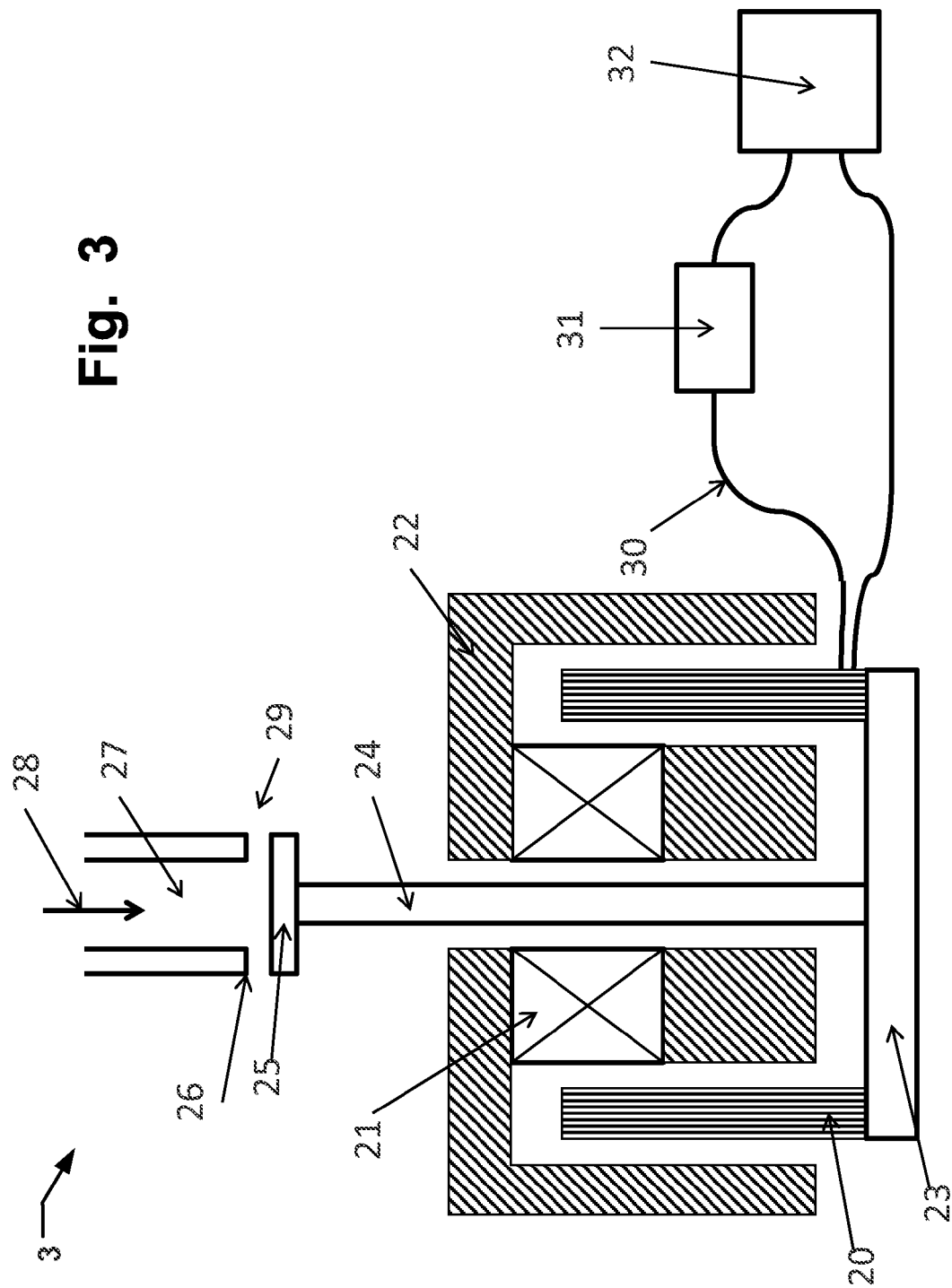
FIG. 3 is illustrating an exemplary implementation of a device for stabilizing a voice coil.

FIG. 3 is illustrating a schematic diagram of a system 3 for the purpose of illustrating certain features and advantages with the device for stabilizing a voice coil disclosed herein.

The system 3 includes voice coil motor and a device for stabilizing a voice coil. The voice coil motor comprises a moveable coil 20 situated within a basically radially oriented magnetic field created by a stationary permanent magnet 21 which together with a soft iron part 22 forms a magnetic circuit.

The diagram depicts only one of many different ways of creating a magnetic circuit. Other configurations of a voice coil motor are possible, for example, the stationary permanent magnet 21 may be placed peripheral to the moveable coil 20. Further examples include configurations wherein the arrangement of the movable coil 20 and the permanent magnet 21 has been switched, or wherein the shaft includes a permanent magnet moving within a coil. Based on the disclosure, the skilled person will be able to appreciate other possible configurations to create a magnetic circuit and a voice coil motor that may be used in the system 3.

The coil is electrically connected with flexible wires 30 via a sensor 31 to a controlling unit 32. The sensor 31 may be a current sensor or a voltage sensor in accordance with the disclosure herein above in connection with FIG. 1 and FIG. 2. If the sensor 31 is a current sensor, the controlling unit 32 generates a set voltage which will create a current in the coil 20. The force acting on the coil 20 is approximately proportional to the current in the coil 20. In addition, the movement of the coil 20 within the magnetic field creates a motional electromotive force (motional EMF) which is a voltage across the coil 20 that creates a current in the coil 20 so that the direction of the force created by this current may be opposite to that of the movement. The motional electromotive force (motional EMF) may be seen as a viscous damping as the force is proportional to the speed of the movement of the coil 20 inside the magnetic field of the voice coil motor.

A force which is directed in the opposite direction of a movement has a stabilizing effect (i.e. damping).

The damping caused by the motional electromotive force is normally not strong enough to stabilize the valve/coil, and it is not possible to adjust the damping coefficient, such as the strength of the dampening.

In the illustrated embodiment, the coil 20 is fixed to a coil holder 23 which in turn is fixed to a shaft 24. The shaft 24 is in contact with a valve 25. This will result that any force on the coil 20 will also be present on the valve 25. This force is balanced by an opposing force on the valve created by the pressure difference between the expiratory pressure in the airway 27 and the pressure downstream of the valve 29. This pressure difference is caused by the pressure drop formed by the expiratory gas flow 28 through the opening between the valve 25 and the valve seat 26.

All examples above are described when a voltage or current is used through the voice coil to provide a movement of either the voice coil or an associated magnet which then generates a motional EMF. The same principle as disclosed herein also applies when an external force generates a movement of either the voice coil or an associated magnet. This movement will generate a motional EMF that can be measured as disclosed in the examples hereinabove. The damping or stabilization is then obtained by controlling a signal through the same voice coil used for measuring a signal related to the generated motional EMF. When controlling the signal through the voice coil a motive fore is provided which can be used to stabilizing the voice coil, such as a voice coil motor. The motive force of the voice coil is in a direction of the measured motional EMF.

While several examples of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used. Also, different method steps than those described above, performing the method by hardware, may be provided within the scope of the disclosure. The different features and steps of the disclosure may be combined in other combinations than those described. The scope of the invention is only limited by the appended patent claims.

The invention claimed is:

1. A device for stabilizing a voice coil that controls a respiration valve in a medical device, comprising:
    a voice coil for providing a motive force;
    means for measuring an error signal from said voice coil related to a motional electromotive force, said error signal being based on a difference between a measured signal and an estimated or calculated steady-state signal; and
    a unit for controlling an amplification of said signal to create and induce an adjustable damping force in said voice coil in a direction of said motional electromotive force.

2. The device according to claim 1, wherein said error signal is measured by measuring a current through said voice coil.

3. The device according to claim 2, wherein a sense resistor is connected in series with said voice coil to measure a voltage, said current is calculated based on said voltage and a resistance of said sense resistor.

4. The device according to claim 2, wherein said error signal is a current error based on a difference between an estimated or calculated current in steady state and a measured current when said voice coil or associated magnet moves.

5. The device according to claim 4, wherein said current error is amplified by changing said set voltage resulting in a change of said current through said voice coil.

6. The device according to claim 5, wherein said error signal is a voltage error based on a difference between a measured or estimated voltage across said voice coil in steady state and a measured voltage when said voice coil or an associated magnet moves.

7. The device according to claim 6, wherein said voltage error is amplified by changing said set current resulting in a change of said voltage across said voice coil.

8. The device according to of claim 1, wherein controlling a set voltage to said voice coil controls said amplified signal.

9. The device according to claim 1, wherein said error signal is measured by measuring a voltage across said voice coil.

10. The device according to claim 1, wherein controlling a set current to said voice coil controls said amplified signal.

11. The device according to claim 1, wherein said controlling of said amplified signal is performed directly or by a pulse-width modulator.

12. The device according to claim 1, wherein a negative gain is used to cancel out or lessen effects of inherent motional electromotive force in said voice coil.

13. The device according to claim 1, wherein a high-pass filter is used to remove DC and low frequency components before amplification of said error signal.

14. The device according to claim 1, wherein said voice coil is arranged to drive said voice coil motor.

15. A method of stabilizing a voice coil, comprising: measuring an error signal related to a motional electromotive force of a voice coil, said error signal being based on a difference between a measured signal and an estimated or calculated signal in steady state; controlling an amplification of said signal to create and induce an adjustable damping force in said voice coil in a direction of said motional electromotive force.

16. The method according to claim 15, wherein said error signal is a current error based on a difference between an estimated or calculated current in steady state and a measured current when said voice coil or an associated magnet moves, or wherein said error signal is a voltage error based on a difference between an estimated or calculated voltage in steady state and a measured voltage when said voice coil or an associated magnet moves.

* * * * *